United States Patent
Rousseau et al.

(10) Patent No.: US 8,561,616 B2
(45) Date of Patent: Oct. 22, 2013

(54) METHODS AND DEVICES FOR THE INDIRECT DISPLACEMENT OF THE HYOID BONE FOR TREATING OBSTRUCTIVE SLEEP APNEA

(75) Inventors: Robert A. Rousseau, Ottsville, PA (US); Kevin S. Weadock, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 732 days.

(21) Appl. No.: 12/257,563

(22) Filed: Oct. 24, 2008

(65) Prior Publication Data

US 2010/0106246 A1 Apr. 29, 2010

(51) Int. Cl.
- *A61F 13/00* (2006.01)
- *A61F 5/56* (2006.01)
- *A61C 5/14* (2006.01)
- *A61B 19/00* (2006.01)

(52) U.S. Cl.
USPC ........... 128/848; 128/846; 128/859; 128/860; 128/898; 602/902

(58) Field of Classification Search
USPC .......... 128/846, 848, 859, 860, 898; 606/151, 606/191, 192, 196, 198; 623/1.15, 1.17, 623/1.2, 9
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |

(Continued)

FOREIGN PATENT DOCUMENTS

| | | |
|---|---|---|
| CN | 2465680 Y | 12/2001 |
| CN | 102198010 A | 9/2011 |

(Continued)

OTHER PUBLICATIONS

Shamsuzzaman, et al., "Obstructive Sleep Apnea; Implications for Cardiac and Vascular Disease", JAMA vol. 290: (14); pp. 1906-1914.

(Continued)

*Primary Examiner* — Michael Brown
*Assistant Examiner* — Brandon L Jackson

(57) ABSTRACT

An implant for treating obstructive sleep apnea includes an elongated body having a central region, a first end, and a second end opposite the first end. The central region of the elongated body engages inframandibular musculature that extends between a mandible and a hyoid bone. The first and second ends of the elongated body are optionally anchored to the mandible. The elongated body is under tension for urging the inframandibular musculature in an inferior direction, which, in turn, pulls the hyoid bone anteriorly for minimizing the likelihood of occurrence of obstructive sleep apnea episodes.

4 Claims, 8 Drawing Sheets

(56) References Cited

U.S. PATENT DOCUMENTS

| | | |
|---|---|---|
| 5,609,559 A | 3/1997 | Weitzner |
| 5,683,417 A | 11/1997 | Cooper |
| 5,704,895 A | 1/1998 | Scott et al. |
| 5,792,067 A | 8/1998 | Karell |
| 5,931,855 A | 8/1999 | Buncke |
| 6,161,541 A | 12/2000 | Woodson |
| 6,241,747 B1 | 6/2001 | Ruff |
| 6,250,307 B1 | 6/2001 | Conrad et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,857,829 B2 | 12/2010 | Kaplan et al. |
| 7,888,119 B2 | 2/2011 | Sugaya et al. |
| 2001/0037133 A1 | 11/2001 | Knudson et al. |
| 2003/0004579 A1 | 1/2003 | Rousseau et al. |
| 2003/0149445 A1 | 8/2003 | Knudson et al. |
| 2003/0149447 A1 | 8/2003 | Morency et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze |
| 2005/0251255 A1 | 11/2005 | Metzger et al. |
| 2005/0267321 A1 | 12/2005 | Shadduck |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Weadock |
| 2010/0037901 A1 | 2/2010 | Rousseau |
| 2010/0080791 A1 | 4/2010 | Rousseau |
| 2010/0106246 A1 | 4/2010 | Rousseau et al. |
| 2010/0108077 A1 | 5/2010 | Lindh |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0163056 A1 | 7/2010 | Tschopp et al. |
| 2010/0211184 A1 | 8/2010 | Rousseau |
| 2010/0234794 A1 | 9/2010 | Weadock |
| 2010/0234946 A1 | 9/2010 | Rousseau |
| 2010/0294284 A1 | 11/2010 | Hohenhorst et al. |
| 2010/0319710 A1 | 12/2010 | Sharkawy et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |

(56) References Cited

U.S. PATENT DOCUMENTS

| | | |
|---|---|---|
| 2012/0245629 A1 | 9/2012 | Gross et al. |
| 2013/0074849 A1 | 3/2013 | Rousseau et al. |
| 2013/0098371 A1 | 4/2013 | Rousseau et al. |

FOREIGN PATENT DOCUMENTS

| | | |
|---|---|---|
| DE | 10245076 A1 | 4/2004 |
| DE | 10245076 B4 | 4/2004 |
| EP | 2145587 A2 | 1/2010 |
| EP | 2517633 A1 | 10/2012 |
| FR | 2651113 A1 | 3/1991 |
| JP | 2003265621 | 9/2003 |
| SU | 927236 B | 5/1982 |
| WO | WO 99/00058 A1 | 1/1999 |
| WO | 0066050 | 11/2000 |
| WO | 0121107 | 3/2001 |
| WO | WO 03/096928 A1 | 11/2003 |
| WO | 2004021870 | 3/2004 |
| WO | WO 2004/021869 A2 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | WO 2005/122954 A1 | 12/2005 |
| WO | 2006012188 | 2/2006 |
| WO | 2006072571 | 7/2006 |
| WO | 2006108145 | 10/2006 |
| WO | WO 2007/056583 A1 | 5/2007 |
| WO | 2007075394 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2008118913 | 10/2008 |
| WO | 2009023256 | 2/2009 |
| WO | 2009036094 | 3/2009 |
| WO | WO 2010/035303 A1 | 4/2010 |
| WO | 2010065341 | 6/2010 |
| WO | WO 2012/041205 A1 | 4/2012 |
| WO | WO 2012/064902 A2 | 5/2012 |

OTHER PUBLICATIONS

Teles et al., "Use of Palatal Lift Prosthesis on Patient Submitted to Maxillectomy: A Case Report", Applied Cancer Res. 2005, vol. 25(3), pp. 151-154.

Vicente et al., "Tongue-Base Suspension in Conjunction with Uvulopapatopharyngoplasty for Treatement of Severe Obstructive Sleep Apnea: Long-term Follow-Up Results", The Laryngoscope, vol. 115(7), pp. 1223-1227 (2006).

Wassmuth et al., "Cautery-assisted palatal stiffening operation for the treatment of obstructive sleep apnea syndrome", Otolaryngology—Head and Neck Surgery, vol. 123(1), pp. 55-60 (Jul. 2000).

Notification of Transmittal of the International Search Report and the Written Opinion of the International Search Authority or the Declaration mailed on Feb. 3, 2010 for; PCT/US2009/051924; International Filing Date: Jul. 28, 2009.

Notification of Transmittal of the International Search Report and the Written Opinion of the International Search Authority or the Declaration mailed on May 25, 2010 for; PCT/US2010/023152; International Filing Date: Apr. 2, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated May 25, 2010 for International Patent Application No. PCT/US2010/025778.

International Search Report dated May 25, 2010 for International Patent Application No. PCT/US2009/065293.

Pang, Kenny et al., "Tongue Suspension Suture in Obstructive Sleep Apnea", Operative Techniques in Otolaryngology, vol. 17, No. 4, Dec. 2006, pp. 252-256.

Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).

U.S. Appl. No. 13/279,384, filed Oct. 24, 2011.

U.S. Appl. No. 13/314,704, filed Dec. 8, 2011.

U.S. Appl. No. 13/247,713, filed Sep. 28, 2011.

International Search Report dated Dec. 29, 2009 for International Patent Application No. PCT/US2009/061455.

International Search Report dated Jan. 21, 2010 for International Patent Application No. PCT/US2009/052110.

International Search Report dated Apr. 29, 2010 for International Patent Application No. PCT/US 2009/065293.

International Search Report dated Jan. 14, 2011 for International Patent Application No. PCT/US2010/052628.

International Search Report dated Jan. 20, 2011 for International Patent Application No. PCT/US2010/052644.

International Search Report dated Jan. 24, 2011 for International Patent Application No. PCT/US2010/052649.

International Search Report dated Feb. 28, 2011 for International Patent Application No. PCT/US2010/059673.

International Search Report dated Apr. 9, 2013 for International Patent Application No. PCT/US2012/061569.

International Search Report dated Apr. 2, 2013 for International Patent Application No. PCT/US2012/067708.

The Pillar Procedure, Restore Medical, Inc., www.restoremedical.com, 2 pp. (2008).

Repose Genioglossus Advancement, INFLUENT Medical, www.influ.ent.com, 1 page (2008).

The Advance System, Aspire Medical, Inc., www.aspiremedical.com, 3 pp. (2008).

Shamsuzzaman, et al., "Obstructive Sleep Apnea; Implications for Cardiac and Vascular Disease", JAMA vol. 290: (14); pp. 1906-1914, Oct. 8, 2003.

Schwartz, et al., "Effects of electrical stimulation to the soft palate on snoring and obstructive sleep apnea", J. Prosthetic Denistry, pp. 273-281 (1986).

Wiltfang, et al., "First results on daytime submandibular elxtrostimulation of suprahyoidal muscles to prevent night-time hypopharyngeal collapse in obstructive sleep apnea syndrome", International Journal of Oral & Maxillofacial Surgery, pp. 21-25 (1999).

Harries, et al., "The Surgical treatment of snoring", Journal of Laryngology and Otology, pp. 1105-1106 (1996).

Huang, et al., "Biomechanics of snoring", Endeavour, vol. 19 (3): pp. 96-100 (1995).

Schwab, et al., "Upper airway and soft tissue changes induced by CPAP in normal subjects", Am. J. Respit. Crit. Care Med., vol. 154, No. 4, Oct. 1996, 1106-1116.

Cole, et al., "Snoring: A Review and a Reassessment", Journal of Otolaryngology, pp. 303-306 (1995).

Database WPI Week 198312, Thomson Scientific, London, GB; AN 1983-D9513K XP 002693421, -& SU 927 236 A1 (Petrozazodsk Univ) May 15, 1982 abstract (see figures 7 & 8).

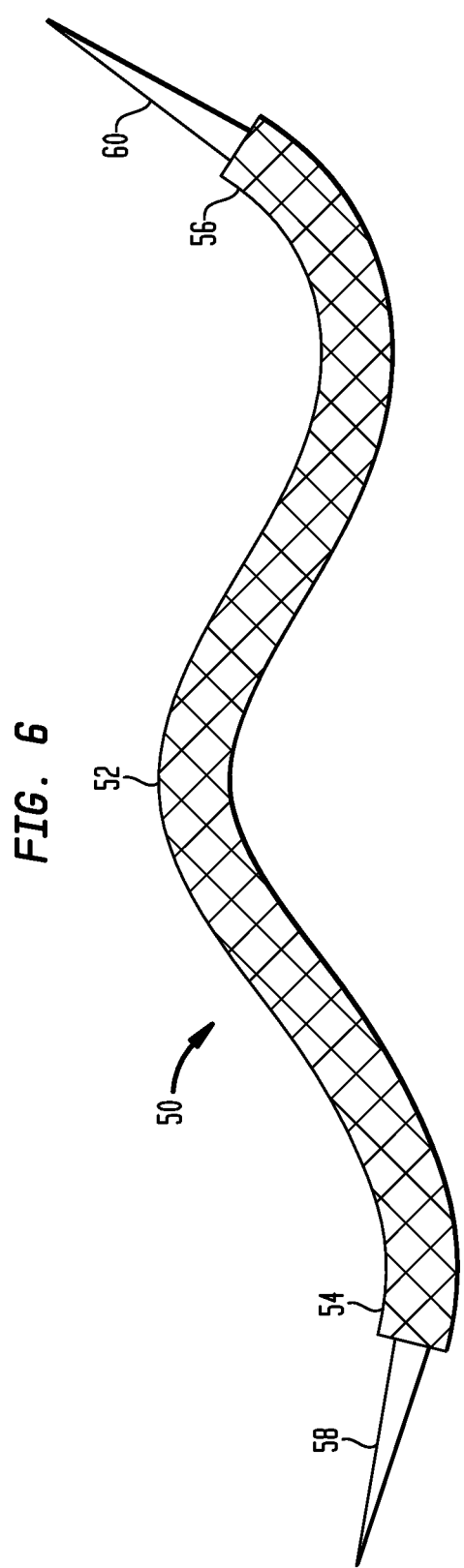

METHODS AND DEVICES FOR THE INDIRECT DISPLACEMENT OF THE HYOID BONE FOR TREATING OBSTRUCTIVE SLEEP APNEA

BACKGROUND OF THE INVENTION

1. Field of the Invention

The present invention generally relates to treating sleep disorders, and more specifically relates to methods and devices for treating patients suffering from obstructive sleep apnea and hypopnea.

2. Description of the Related Art

Obstructive sleep apnea (OSA) is caused by a blockage of the airway, which usually occurs when the soft tissue in the throat collapses and closes during sleep. During each apnea event, the brain briefly arouses the sufferer in order to initiate the resumption of breathing, however, this type of sleep is extremely fragmented and of poor quality. When left untreated, OSA may result in high blood pressure, cardiovascular disease, weight gain, impotency, headaches, memory problems, job impairment, and/or motor vehicle crashes.

According to the National Institutes of Health, OSA is rather common and affects more than twelve million Americans. OSA affects males more than females. Other risk factors include being overweight and over the age of forty, however, OSA can strike anyone at any age, even children. Despite the seriousness of OSA, a lack of awareness by the public and healthcare professionals results in the vast majority of patients remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and result in repeated arousal of the patient.

Another protocol for treating OSA, continuous positive airway pressure (CPAP), delivers air into the airway through a specially designed nasal mask or pillow. The flow of air creates positive pressure when the patient inhales to keep the airway open. CPAP is considered by many to be the most effective non-surgical treatment for the alleviation of snoring and obstructive sleep apnea, however, patients complain about discomfort from the mask and hoses, including bloating, nasal drying, and dry eyes. As a result, patient compliance is only about 40%.

Surgical treatments have also been employed. One such treatment is referred to as uvulopalatopharyngoplasty, which involves removing about 2 cm of the trailing edge of the soft palate to reduce the soft palate's ability to flutter between the tongue and the pharyngeal wall of the throat. The procedure has been effective in alleviating snoring, but is painful and frequently results in undesirable side effects. In particular, removal of the trailing edge of the soft palate compromises the soft palate's ability to seal off nasal passages during swallowing and speech. As a result, many uvulopalatopharyngoplasty patients experience fluid escaping from the mouth and flowing into the nose while drinking.

Another procedure uses a surgical laser to create scar tissue on the surface of the soft palate. The scar tissue reduces the flexibility of the soft palate, which, in turn, reduces snoring and/or closing of the air passage. The above-mentioned laser procedure may have limited utility in treating snoring, but is ineffective in treating OSA.

Cautery-assisted palatal stiffening operation (CAPSO) is a recently developed office-based procedure performed with local anesthesia. A midline strip of soft palate mucosa is removed, and the wound is allowed to heal. The flaccid palate is stiffened, and palatal snoring ceases. As with the previously discussed surgical approaches, this procedure is not effective in treating OSA.

Surgical procedures such as uvulopalatopharyngoplasty and those mentioned above continue to have problems. The area of surgical treatment (i.e., removal of palatal tissue or scarring of palatal tissue) may be inappropriate to treat the patient's condition. In addition, the proposed procedures are painful with extended and uncomfortable healing periods. For example, scar tissue on the soft palate may present a continuing irritant to the patient. Moreover, the procedures are not reversible in the event they happen to induce adverse side effects. Finally, the procedures are useful in some patients experiencing snoring, but have little beneficial effect on patients with OSA.

Other surgical approaches have been tried that employ the use of RF or microwave energy (Somnoplasty) to shrink tissue in the tongue or soft palate. Radiofrequency ablation of the soft palate is used to produce thermal lesions within the tissues. Somnoplasty devices have been approved by the U.S. Food and Drug Administration (FDA) for radiofrequency ablation of palatal tissues for simple snoring and for the base of the tongue for OSA. In some situations, radiofrequency of the soft palate and base of tongue are performed together as a multilevel procedure. To date, the treatments alone or in combination have failed to provide relief to more than 50% of patients.

Another device intended to treat snoring or obstructive sleep apnea uses several braided PET cylinders that are implanted to make the tissues of the tongue or uvula more rigid and less prone to deflection. The Pillar™ Palatal Implant System sold by Restore Medical of St. Paul, Minn. is an implantable device that has been cleared by the FDA. The device is a cylindrical-shaped segment of braided polyester filaments that is permanently implanted submucosally in the soft palate, for reducing the incidence of airway obstructions in patients suffering from mild to moderate obstructive sleep apnea. The Pillar device has been associated with a number of adverse side effects, including extrusion, infection, and patient discomfort.

Another implant system sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension, or hammock, of the tongue base making it less likely for the base of the tongue to prolapse during sleep. Due to the high activity of the tongue during wakefulness, the suture component of this device may act as a "cheese cutter" to the tongue, causing device failure and requiring subsequent removal.

One effort for treating OSA involves creating an auxiliary airway. In one embodiment, commonly assigned U.S. patent application Ser. No. 12/182,402, filed Jul. 30, 2008, the disclosure of which is hereby incorporated by reference herein, teaches forming an auxiliary airway for treating obstructive sleep apnea by implanting an elongated conduit beneath a pharyngeal wall of the pharynx. The elongated conduit has a proximal end in communication with a first region of the pharynx, a distal end in communication with a second region of the pharynx, and a section extending beneath the pharyngeal wall for bypassing an oropharynx region of the pharynx.

Magnets have also been used for treating sleep apnea. For example, in one embodiment, commonly assigned U.S. patent application Ser. No. 12/183,955, filed Jul. 31, 2008, the disclosure of which is hereby incorporated by reference herein, discloses a magnetic implant including a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets.

In spite of the above advances, there remains a need for additional methods and devices for reducing the burden of managing obstructive sleep apnea through minimally invasive approaches that provide long term results, that encourage patient compliance, and that minimize patient discomfort.

SUMMARY OF THE INVENTION

In one embodiment, an implant is used for the indirect displacement of the hyoid bone through the inferior, lateral, and/or superior displacement of the inframandibular musculature. In one embodiment, inferior displacement preferably results in the musculature being pushed downwards toward the lower extremities of the patient. In one embodiment, lateral displacement preferably results in the musculature being pushed laterally toward the sides of the patient. In one embodiment, superior displacement preferably results in the musculature being pushed upwards toward the upper end of the patient. The inframandibular muscular generally refers to the geniohyoid, mylohyoid, digastric, and pterygoid muscles. In one embodiment, the location of hyoid bone is altered through the use of an implant device that is placed superior to the mylohyoid muscle. The implant device is preferably anchored to the lower anterior and posterior aspects of the mandible to inferiorly displace the inframandibular musculature which, in turn, shifts the hyoid bone in an anterior direction for avoiding obstructive sleep apnea events. In other preferred embodiments, the implant device displaces the inframandibular musculature in a lateral or superior direction, which, in turn, shifts the hyoid bone in an anterior direction.

In one embodiment, an implant for treating obstructive sleep apnea includes an elongated body having a central region, a first end, and a second end opposite the first end. The central region of the elongated body preferably engages the geniohyoid musculature that extends between a mandible and a hyoid bone. As used herein, the terms "engages" or "engaging" mean to couple with, interlock with, contact, secure, and/or attach. The first and second ends of the elongated body are preferably anchored to the opposing lateral aspects of the mandible, whereby the elongated body is under tension for urging the inframandibular musculature in an inferior direction. As the geniohyoid and inframandibular musculature is urged in an inferior direction, tension is applied to the hyoid bone in an anterior direction. As the hyoid bone is advanced, the tongue base is also displaced anteriorly for avoiding obstructive sleep apnea events.

In one embodiment, the elongated body is a biocompatible mesh. The implant may include a tissue piercing element secured to one of the ends of the elongated body. As used herein, the terms "secure", "securing" and "secured" mean fasten, attach, join, fix, clip, connect, couple and/or tie. The elements described herein may be secured together using knots, glue, or any other fastening methods or fasteners known to those skilled in the art. In one embodiment, the implant includes a first tissue piercing element secured to the first end of the elongated body and a second tissue piercing element secured to the second end of the elongated body.

In one embodiment, the implant includes an inflatable bladder located in the central region of the elongated body. The inflatable bladder may overlie the elongated body or may be embedded within the elongated body. The inflatable bladder desirably includes a port for filling the inflatable bladder with a liquid, gel, or a gas. The inflation level of the inflatable bladder may be adjusted in response to the desired level of inferior displacement of the inframandibular musculature.

In one embodiment, the first end of the elongated body is desirably anchored to a first outer surface region of the mandible and the second end of the elongated body is anchored to a second outer surface region of the mandible that faces away from the first outer surface region of the mandible. Tension is desirably applied to the first and second ends of the elongated body and, while maintaining the tension on the elongated body, the first and second ends are anchored to the mandible. As used herein, the terms "tension" or "tensioning" mean applying a force tending to stretch or elongate an object.

Although the present invention is not limited by any particular theory of operation, it is believed that the implanted elongated body will urge the inframandibular musculature in an inferior direction. In turn, as the musculature is coupled with the hyoid bone, inferior displacement of the musculature will result in the hyoid bone being displaced in an anterior direction. As the hyoid bone is displaced in an anterior direction, the likelihood of an obstructive sleep apnea event occurring is minimized.

In one embodiment, an implant for treating obstructive sleep apnea includes an elongated body having a central region, a first end, and a second end opposite the first end. The central region of the elongated body is adapted to engage the inframandibular musculature that extends between an inner surface of the mandible and a hyoid bone. The first end of the elongated body is preferably secured to a first outer surface region of the mandible, and the second end of the elongated body is preferably secured to a second outer surface region of the mandible. The elongated body is desirably under tension so as to inferiorly displace the inframandibular musculature. The central region of the elongated body preferably engages a mylohyoid muscle or a geniohyoid muscle for providing the force for inferiorly displacing the inframandibular musculature.

In one embodiment, the elongated body comprises a flexible, biocompatible mesh. The elongated body may also include an inflatable bladder located in the central region thereof, whereby the inflatable bladder is adapted to receive a liquid or a gas for selectively inflating the bladder.

In one embodiment, a method for treating obstructive sleep apnea includes inferiorly displacing the inframandibular musculature having an anterior end coupled with an inner surface of a mandible and a posterior end coupled with a hyoid bone for anteriorly displacing the hyoid bone. In one embodiment, the step of inferiorly displacing musculature includes providing an implant having an elongated body with a central region, a first end and a second end opposite the first end. The inframandibular musculature is preferably engaged with the central region of the implant. After engaging the inframandibular musculature, the first and second ends of the elongated body are placed under tension for inferiorly displacing the inframandibular musculature. After tensioning, the first and second ends of the elongated body are desirably fixed to the mandible. The fixing of the first and second ends to the mandible may include anchoring the first end of the elongated body to a first outer surface region of the mandible and anchoring the second end of the elongated body to a second outer surface region of the mandible. In one embodiment, one or more of the ends of the implant may be passed through the mandible and secured to washer-like devices on the exterior surfaces of the mandible.

These and other preferred embodiments of the present invention will be described in more detail below.

BRIEF DESCRIPTION OF THE DRAWING

FIG. 6 shows an implant device for the indirect displacement of a hyoid bone for treating obstructive sleep apnea, in accordance with one embodiment of the present invention.

DETAILED DESCRIPTION

Figure 1:
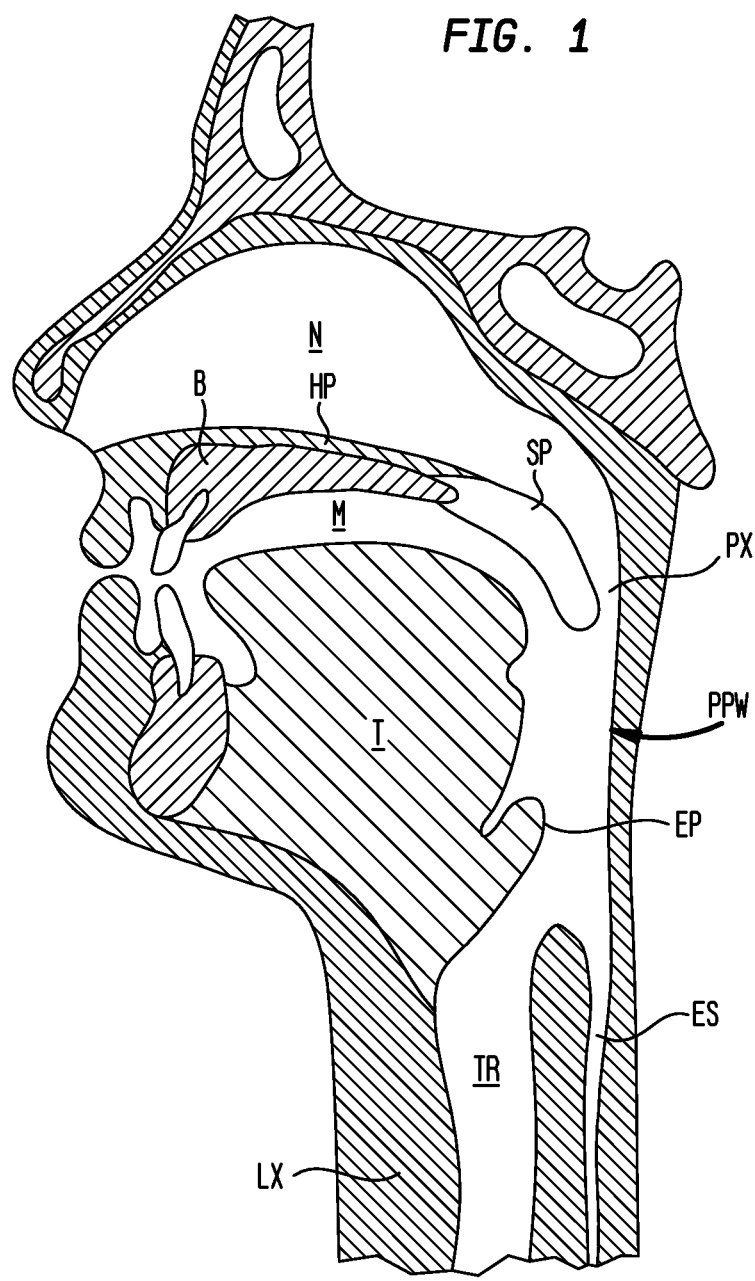
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW.

Figure 2:
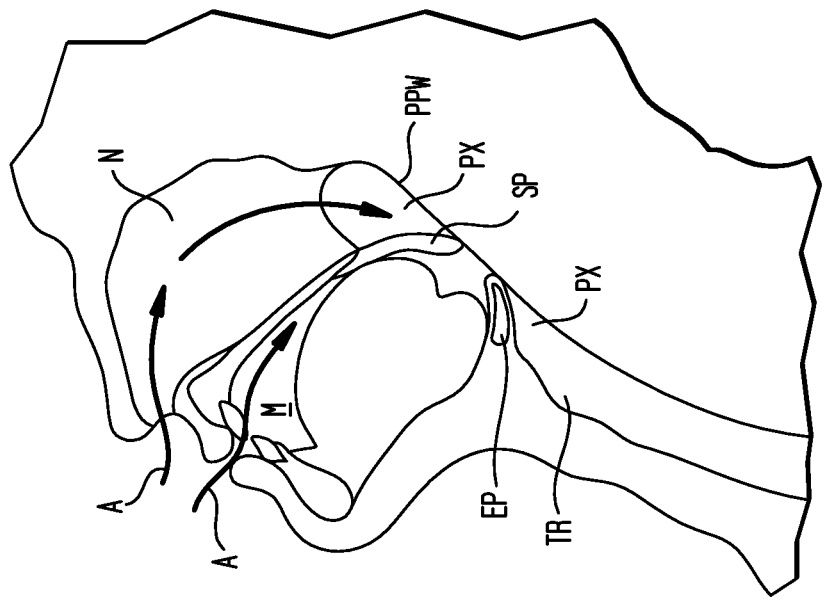
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both very flexible structures. The soft palate SP provides a barrier between the nasal cavity N and the mouth M. In many instances, the soft palate SP is longer than necessary so that it extends a significant distance between the back of the tongue T and the posterior pharyngeal wall PPW.

Figure 3:
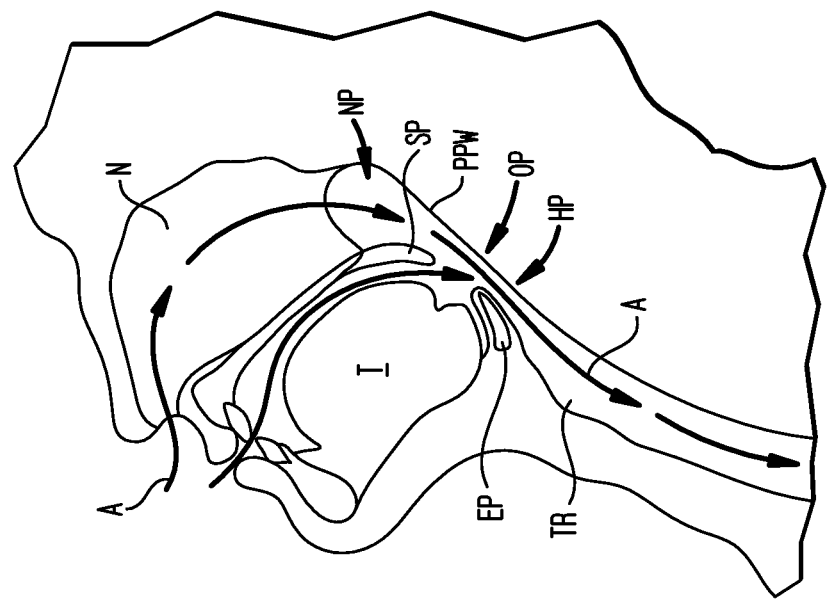
FIG. 3 shows a cross-sectional view of the nasal cavity and the pharynx of a human during an episode of obstructive sleep apnea.

Referring to FIG. 2, when an individual is awake, the back of the tongue T and the soft palate SP maintain their shape and tone due to their respective internal muscles and neural stimuli. As a result, the airway A through the pharynx remains open and unobstructed. During sleep the muscle tone decreases so that the back of the tongue and the soft palate become more flexible and distensible. Referring to FIG. 3, within those people having OSA, the lack of muscle tone causes the tongue T, the epiglottis EP, or soft palate SP to easily collapse to block the airway A.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW or lateral pharyngeal wall to block airflow into the trachea. As the airway narrows, airflow through the pharynx and nasal cavity may become turbulent, causing the soft palate SP to vibrate and generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occur more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

The present invention provides a number of advantages over prior art methods and devices used for treating obstructive sleep apnea syndrome and hypopnea. First, the methods and devices disclosed herein provide for simple surgical procedures that are minimally invasive. Typically, the methods and devices disclosed herein may be utilized during an outpatient procedure. In addition, the methods and devices disclosed herein provide both immediate and long term results for treating obstructive sleep apnea syndrome and hypopnea. Moreover, the methods and devices disclosed herein do not require a significant level of patient compliance.

Figure 4:
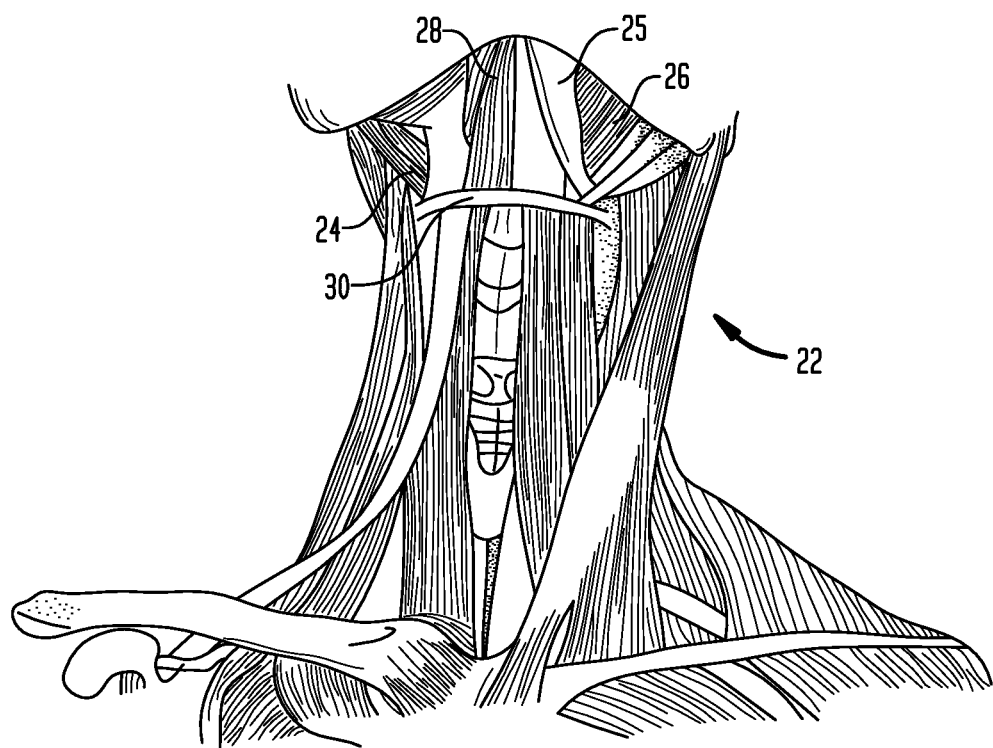
FIG. 4 shows the musculature of a human in the neck region.

Referring to FIG. 4, in one embodiment, a human patient 20 has a neck region 22 including musculature located in the floor 24 of an oral cavity. In particular, the musculature in the inframandibular region includes the digastrics 25, mylohyoid 26 and the geniohyoid muscles 28 that provide partial displacement of a hyoid bone 30. The mylohyoid muscles 26 and the geniohyoid muscles 28 generally form the bulk of the muscular floor of the oral cavity. The mylohyoid and the geniohyoid muscles function independently of one another, however, both muscles alter the position of the hyoid bone 30 during swallowing and speech. The tongue, not shown, is located above both the mylohyoid 26 and geniohyoid muscles 28 and contains the genioglossus muscle.

Figure 5:
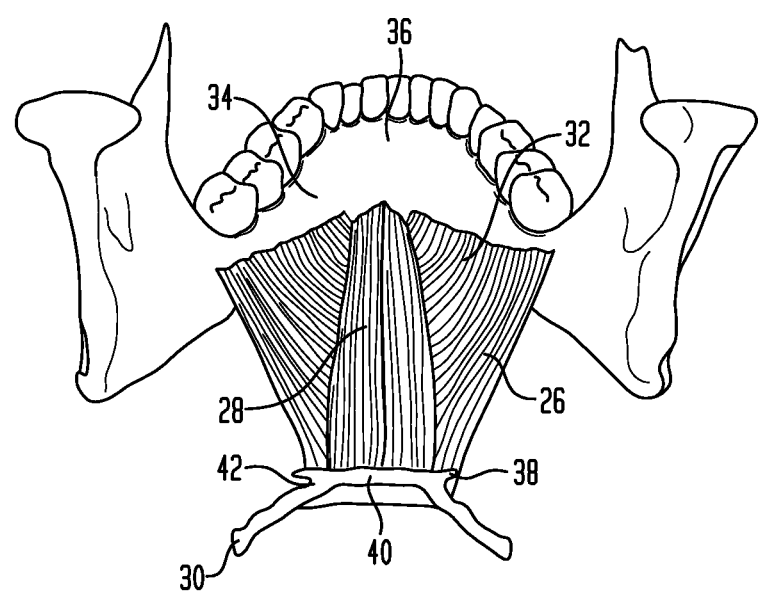
FIG. 5 shows a superior view of the inframandibular musculature of a human.

Referring to FIG. 5, the mylohyoid muscle 26 has an anterior end 32 that is anchored to the inner margin 34 of the mandible 36, and a posterior end 38 that is fixed to the central superior section 40 and the anterior aspects 42 of the hyoid bone 30. Thus, the mylohyoid musculature 26 couples the hyoid bone 30 with the mandible 36. The geniohyoid muscle 28 is superior to the mylohyoid muscle and also couples the hyoid bone 30 with the inner margin 34 of the mandible 36. During activation of the mylohyoid and geniohyoid muscles 26, 28, the hyoid bone 30 is tensioned and lifted, and the floor of the mouth is lifted slightly. As will be described in more detail below, a similar physical connection exists between the digastrics muscles and the hyoid bone.

Referring to FIG. 6, in one embodiment, an implant device is used for the indirect displacement of a hyoid bone by the inferior displacement of the musculature of the oral cavity, such as the inframandibular musculature. In one embodiment, the implant device 50 is used for treating obstructive sleep apnea and includes a central region 52, a first end 54, and a second end 56. In one embodiment, the implant device is biocompatible, and non-resorbable. In preferred embodiments, the implant device 50 may be made of a wide range of biocompatible materials including polymeric mesh comprised of polypropylene, polyethylene, polytetrafluoroethylene (PTFE), expanded polytetrafluoroethylene (having internodal distances of 15-250 microns), silicone, polyurethane and any other biocompatible polymers known to those skilled in the art of medical implants. Alternatively, the implants may be formed of non-polymeric mesh like elastic materials such as nitinol, titanium and other elastic materials that provide force to the tissue to be displaced. The invention is not limited to non-resorbable materials, as cross-linked collagen films or meshes may also be used. In one embodiment, the implant material 50 includes a first tissue piercing element 58 secured to the first end 54 thereof and a second tissue piercing element 60 secured to the second end 56 thereof. The tissue piercing elements 58, 60 are adapted to pass through tissue and musculature. In one embodiment, the tissue piercing elements 58, 60 are needles or rods having pointed ends.

Figure 7A:
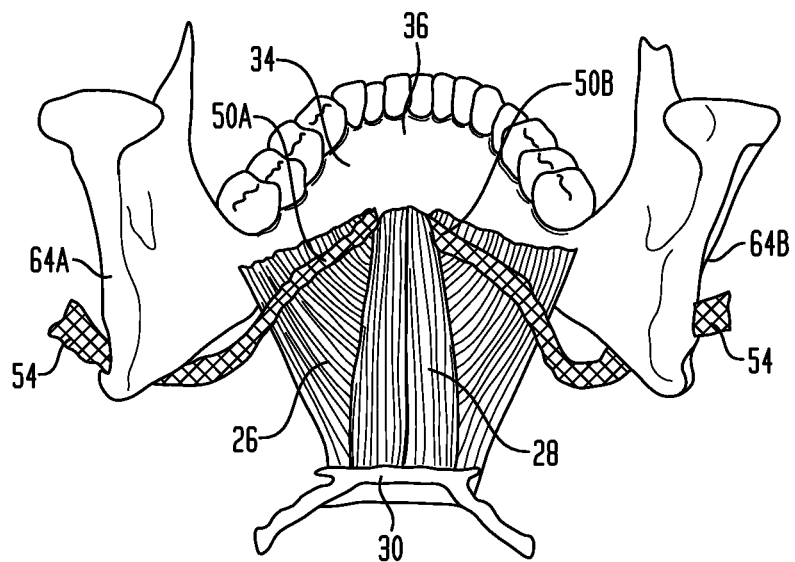
FIG. 7A shows a superior view of the inframandibular musculature of a human after implantation of the device of FIG. 6 for suspending a hyoid bone, in accordance with one embodiment of the present invention.

Referring to FIG. 7A, in one embodiment, the implant device 50 is desirably positioned above the mylohyoid musculature 26 and below the geniohyoid musculature 28. In one embodiment, the implant device 50 may be positioned above both the mylohyoid and the geniohyoid muscles. In one preferred embodiment, the central region 52 of the implant device 50 is positioned adjacent the inner margin 34 of the mandible 36, and preferably conforms to the shape of the inner margin 34 of the mandible. The conformance of the implant device 50 to the shape of the mandible is preferably symmetrical.

In one embodiment, an implant device as described herein is looped around the geniohyoid or digastrics and has both ends of the implant device anchored at the same or approximately the same location on the lateral edge of the mandible thereby causing inferior, lateral, and/or superior displacement of the digastrics or geniohyoid musculature.

Figure 7B:
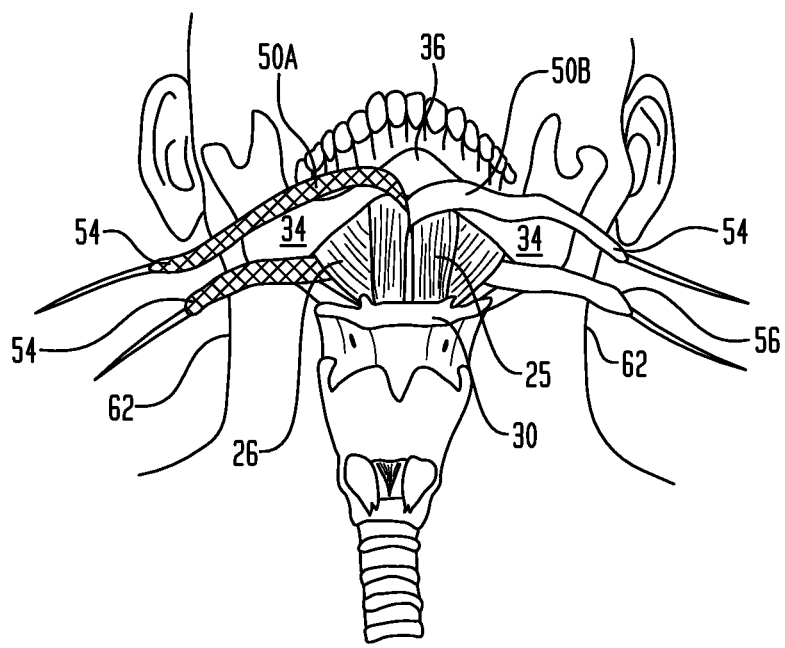
FIG. 7B shows an inferior view of the inframandibular musculature of a human after implantation of the device of FIG. 6, in accordance with one embodiment of the present invention.

Referring to FIGS. 7A and 7B, in one embodiment, a pair of implant devices 50A, 50B are used, and each implant device is passed between the digastric muscles 25, parallel to the inner surface 34 of the mandible 36, and superior to the mylohyoid muscle 26. FIG. 7A depicts the geniohyoid located within the inframandibular region and is superior to the mylohyoid muscle. FIG. 7B illustrates the pair of implant devices 50A, 50B placed superior to the mylohyoid muscle 26 and exiting between the digastrics 25 at the anterior location of the mandible. The respective first and second ends 54, 56 of the two implanted devices 50A, 50B may exit along the inferior surface of the mandible 36, posterior to the region where the mylohyoid musculature 26 is anchored to the mandible 36. The first and second ends 54, 56 of the implant devices 50A, 50B are preferably passed superiorly along the mylohyoid musculature 26 and inferior to the edge of the mandible 36. In one embodiment, at least one of the implant devices 50A, 50B preferably exits through skin 62 at the approximate locations as shown in FIG. 7B. For the sake of clarifying, the positioning of the implant devices 50A, 50B relative to the musculature, the non-muscular layers and the soft tissues has not been included in the illustration.

In one embodiment, the ends of the implants 50A, 50B are fixed to the inferior edge of the mandible 36 while being accessed through the use of a small incision. Tension is preferably applied to the first and second ends 54, 56 of the implant device 50 in order to displace the mylohyoid musculature 26. In one embodiment, the musculature is displaced inferiorly, however, the musculature may also be displaced superiorly, laterally, or combinations thereof (e.g. laterally and inferiorly). Once a preferred level of tension is applied to the first and second ends 54, 56 of the implant devices 50A, 50B, the first and second ends are fixed to the mandible 36. Fixation may be accomplished using sutures, suture anchors, or adhesives such as cyanoacrylate or fibrin glue for securing the first and second ends of the implant to the respective outer surfaces 64A, 64B of the mandible 36. Alternatively, the ends 54, 56 of the implant devices 50A, 50B may be passed through surgically created holes in the mandible and then secured on the outside of the mandible with anchoring elements such as a locking sleeve, a slotted spring washer type device, sutures, adhesives, and/or a staple.

Although the present invention is not limited by any particular theory of operation, it is believed that implanting a device as shown and described above in FIGS. 7A-7B will shorten the distance between the insertion points of the mylohyoid musculature due to the inferior, lateral, and/or superior displacement of the musculature. As a result of the displacement of the mylohyoid musculature 26, the hyoid bone 30 will be displaced in an anterior direction, which provides more space in the airway. During the course of healing, the implant device preferably stimulates a tissue response and the insertion points of the mylohyoid musculature are effectively repositioned at the edge of the mandible. As a result, the hyoid bone 30 is displaced slightly anteriorly and inferiorly to accommodate the shortened mylohyoid musculature. Displacing the hyoid bone 30 in an anterior and inferior direction will minimize the occurrence of obstructive sleep apnea events.

Figure 8:
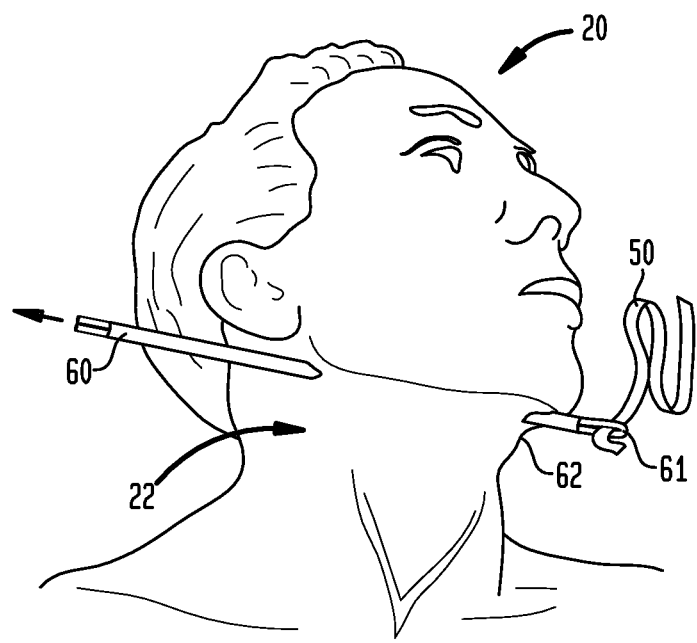
FIG. 8 shows a perspective view of a patient during a surgical procedure for implanting the implant device of FIG. 6.

FIG. 8 shows an implant device 50, such as the implant devices shown in FIGS. 6-7B, being implanted in the neck region 22 of a human 20. In one embodiment, the ends of the implant device have tissue piercing elements secured thereto so that the implant device 50 may be passed through the tissue and skin 62 of the patient 20 during an implantation procedure. In one embodiment, the tissue piercing element is preferably a sharpened metal or polymeric device that is coupled on one end to the mesh component. In one embodiment, the tissue piercing element 60 may be provided with a receiving geometry 61, such as an eyelet or snare, that is utilized to draw the implant 50 through the dissected tissue tract upon withdrawal of the piercing element 60.

Figure 9A:
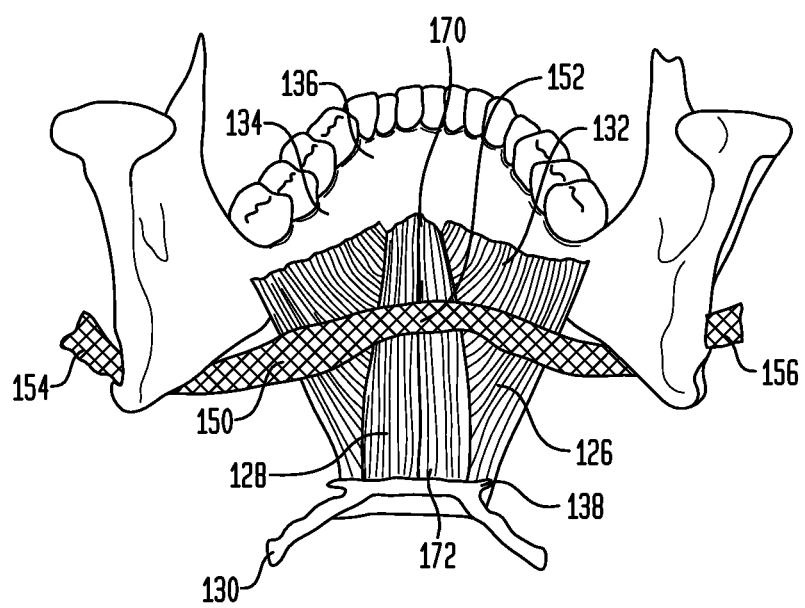
FIGS. 9A-9C show an implant device for suspending a hyoid bone, in accordance with one embodiment of the present invention.

Referring to FIG. 9A, in one embodiment, an implant device 150 includes a central region 152, a first end 154, and a second end 156. The implant device 150 may have one or more of the properties as the implant devices described above in FIGS. 6 and 7A-7B. The musculature of the inframandibular region includes the mylohyoid muscles 126, the geniohyoid muscles 128, and the digastrics (not shown but highlighted by reference number 25 in FIG. 7B). The mylohyoid musculature 126 has an anterior end 132 secured to the inner face 134 of the mandible 136 and a posterior end 138 secured to the hyoid bone 130. The geniohyoid musculature 128 has an anterior end 170 secured to the inner face 134 of the mandible 136 and a posterior end 172 secured to the hyoid bone 130. In the embodiment of FIG. 9A, the implant device 150 passes superior to the geniohyoid muscle 128 and is used to displace the geniohyoid muscle in an inferior direction. The implant device 150 is preferably implanted through an intra-oral route that exits through the skin below the mandible 136.

Figure 9B:
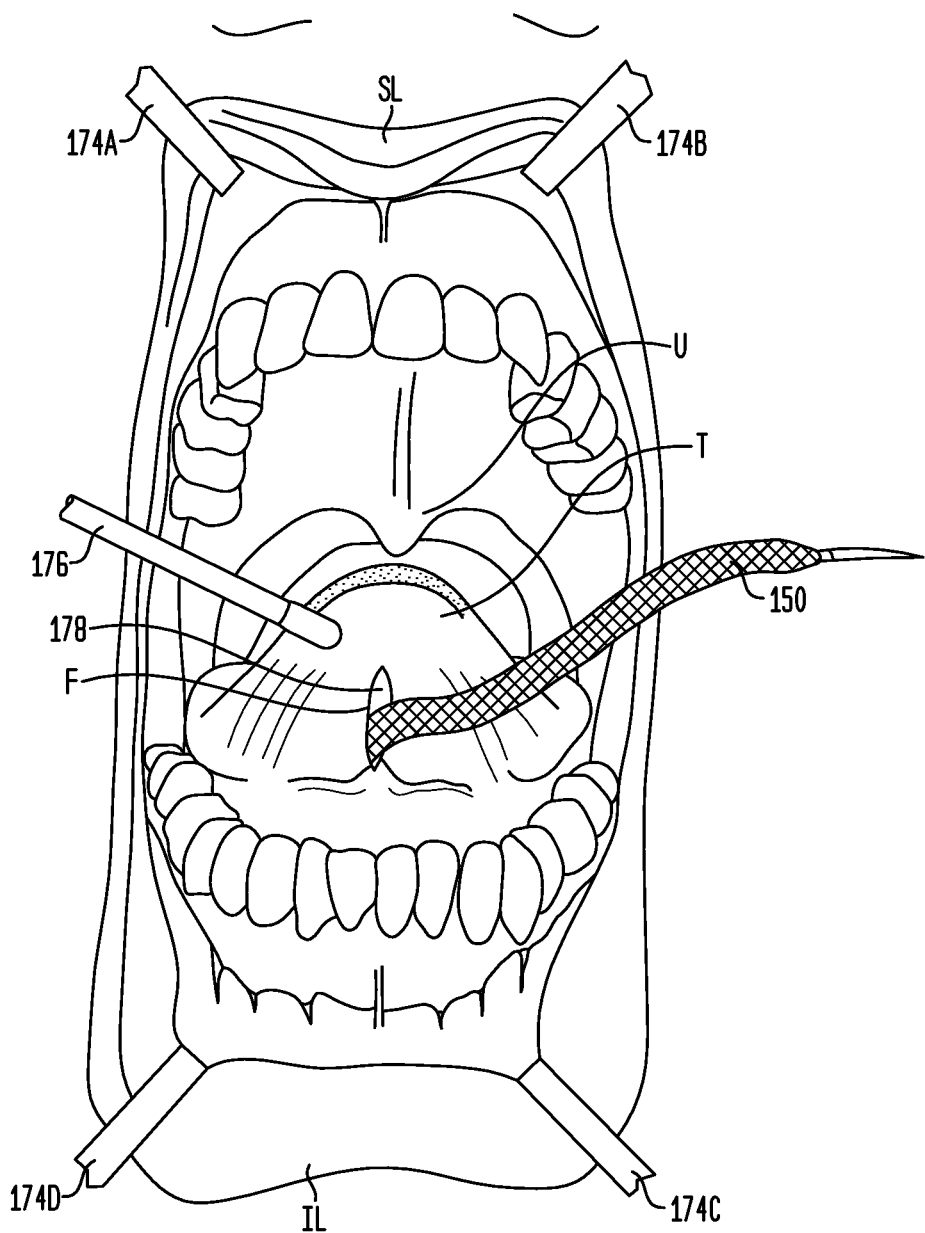

Referring to FIG. 9B, in one embodiment, the implant device 150 is preferably implanted in the inframandibular musculature 124 of a patient 120. In one embodiment, four retractors 174A-174D are used to apply tension to a superior lip SL and an inferior lip IL of the patient 120 to provide access to the oral cavity 124. The tongue T is retracted posteriorly into the oral cavity towards the uvula U using a tongue retractor 176 or a grasping device for exposing the frenulum F. In one embodiment, an incision 178 is made in the base of the tongue T, near the frenulum F. The respective ends of the implant device 150 are preferably passed into the incision 178 in the base of the tongue T and are passed laterally, submucosally, to cross the floor of the oral cavity. The first and second ends of the implant device are desirably passed through a gap within the muscle fibers of the mlyohyoid musculature and are passed below the lower lateral edges of the mandible. In one embodiment, the first and second ends of the implant device are preferably passed slightly posterior to the location where the mylohyoid musculature is attached to the edge of the mandible. The first and second ends of the implant device are preferably passed inferior to the lower edge of the mandible and tension is preferably applied to the first and second ends of the mandible. The tensioning of the implant device causes an inferior displacement and/or depression of the geniohyoid muscle, which, in turn, causes tension and a slight anterior motion of the hyoid bone resulting in the anterior displacement of the tongue base.

Figure 9C:
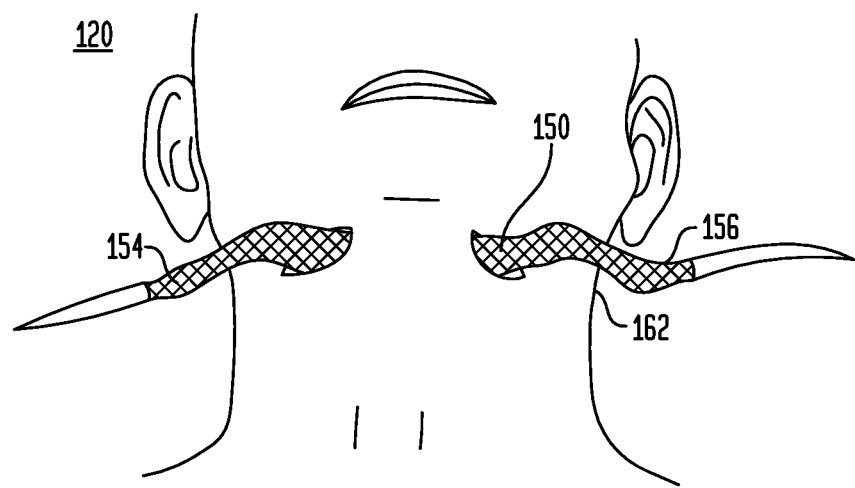

In one embodiment, the implant device is preferably placed within a plane that lies between the genioglossus and the geniohyoid muscles. The implant device preferably provides an anchoring point to the base of the tongue as healing occurs. FIG. 9C shows the first and second ends 154, 156 of the implant device 150 being passed through the skin 162 of a patient 120.

Although the present invention is not limited by any particular theory of operation, it is believed that using an implant device to suspend the geniohyoid musculature as shown and described above in FIGS. 9A-9C will shorten the distance between the insertion point of the geniohyoid muscle, or the geniotubercle, located on the inframandibular portion of the anterior mandible, and the hyoid bone through redirection of the tissue plane between the genioglossus and the geniohyoid. In addition, after implantation of the device, the displacement device preferably elicits a tissue response that causes the formation of a scar tissue bond between the device and the genioglossus and geniohyoid muscles. The formation of the scar tissue preferably further limits the extent of motion of the tongue base when the tongue is in a relaxed condition.

In one embodiment, an implant device as described herein is looped around the geniohyoid or digastrics and has both ends of the implant device anchored at the same or approximately the same location on the lateral edge of the mandible thereby causing inferior, lateral, and/or superior displacement of the digastrics or geniohyoid musculature. In one preferred embodiment, the displacement is inferior, however, in other embodiments the displacement may be lateral, lateral and inferior, lateral and superior, and/or superior. Although the present invention is not limited by any particular theory of operation, it is believed that using the implants described herein for displacement of the digastrics or geniohyoid muscles will move the back of the tongue and surrounding tissue away from the opposing pharyngeal wall for minimizing the likelihood of OSA episodes.

Figure 10:
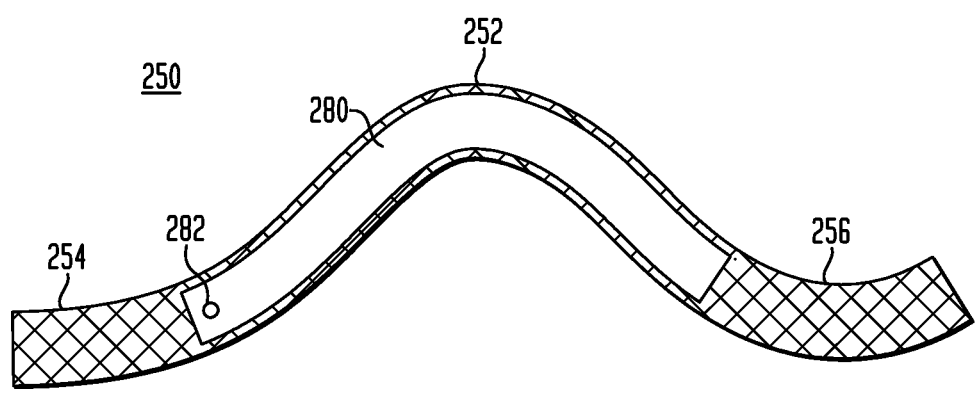
FIG. 10 shows an implant device for treating obstructive sleep apnea, in accordance with one embodiment of the present invention.

Referring to FIG. 10, in one embodiment, an implant device 250 for treating obstructive sleep apnea includes a central region 252, a first end 254, and a second end 256. The implant device preferably forms a flexible, elongated, biocompatible strip that may be used for the inferior displacement of the inframandibular musculature so as to provide for the indirect displacement of a hyoid bone.

The implant device 250 preferably includes a bladder 280 that is carried by a flexible, biocompatible strip. The bladder 280 is desirably inflatable and is preferably placed over or embedded within the central region 252 of the implant device 250. The inflatable bladder 280 desirably includes an inflation port 282 that may be used for inflating the bladder with a solution such as a sterile saline solution. The bladder may be comprised of a biocompable elastomer such as silicone, polyurethane, or other materials known to those skilled in the art of making balloons for use on medical implants. The inflation port may optionally be connected to another, smaller bladder placed subcutaneously by a small tube in communication with both bladders. The physician may therefore adjust the volume of the main bladder through an injection in the neck, whereby the injection is aimed at the smaller bladder in the subcutaneous space. The inflatable bladder 280 may also be inflated with a gas. In one embodiment, a sterile needle is preferably inserted into the inflation port 282, and a gas or liquid is introduced into the bladder 280 for inflating the bladder. Although the present invention is not limited by any particular theory of operation, it is believed that the implant device shown and described in FIG. 10 enables the treatment of obstructive sleep apnea to be titratable whereby the tension on the musculature at the base of the oral cavity may be adjusted by inflating or deflating the bladder 280.

In one embodiment, after an incision is made in the frenulum, the genioglossus muscle may be undermined by using a scalpel or harmonic scalpel. The genioglossus muscle may be repositioned anteriorly to a point that opens the airway sufficient for normal breathing. The implant device is desirably implanted through the plane created to advance the genioglossus muscle. After anterior displacement of the genioglossus muscle, the newly positioned genioglossus muscle may be sutured to the implant device or surrounding tissue. In this embodiment, the implant device may be used as part of a two-part system whereby the mesh is also adapted to indirectly displace the hyoid bone. The above-described methods and devices may also be used alone.

The present invention discloses a simple, minimally invasive procedure that may be performed on an out-patient basis.

The present invention desirably provides immediate and long-term results for treating obstructive sleep apnea. The present invention does not impact the shape or motion of the tongue or soft palate, but only indirectly affects the position of the hyoid bone. Thus, the present invention is less likely to affect swallowing or speech, thereby providing a great improvement over prior art devices and methods. The present invention also preferably uses materials having long-term biocompatibility.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Although various embodiments disclosed herein relate to use in humans, it is contemplated that the present invention may be used in all mammals, and in all animals having air passages. Moreover, the methods and devices disclosed herein may incorporate any materials that are biocompatible, as well as any solutions or components that minimize rejection, enhance tissue ingrowth, enhance the formation of mucosal layers, and/or improve acceptance of the implant device by a body after the device has been implanted.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A method of treating obstructive sleep apnea comprising using an implant for displacing inframandibular musculature by direct contact having an anterior end coupled with an inner surface of a mandible and a posterior end coupled with a hyoid bone for anteriorly displacing the hyoid bone;
   wherein the displacing inframandibular musculature step comprises:
      providing an implant including an elongated body having a central region, a first end, and a second end opposite the first end;
      engaging the inframandibular musculature with said elongated body;
      tensioning the first and second ends of said elongated body for displacing the inframandibular musculature;
   the method further comprising after tensioning the first and second ends of said elongated body, fixing the respective first and second ends of said elongated body to the mandible;
   wherein the fixing the first and second ends step comprises anchoring the first end of said elongated body to a first outer surface region of the mandible and anchoring the second end of said elongated body to a second outer surface region of the mandible.

2. The method as claimed in claim 1, wherein the displacing inframandibular musculature comprises inferiorly displacing, superiorly displacing, or laterally displacing the inframandibular musculature.

3. The method as claimed in claim 1, wherein said elongated body comprises a flexible, biocompatible material.

4. The method as claimed in claim 1, wherein the inframandibular musculature is selected from the group consisting of the mylohyoid, digastric, pterygoid, and the geniohyoid muscles.

* * * * *